United States Patent [19]

Zimmer

[11] Patent Number: 4,459,785

[45] Date of Patent: Jul. 17, 1984

[54] CHUCK FOR VERTICALLY HUNG SPECIMEN HOLDER

[75] Inventor: Robert E. Zimmer, Niles, Ill.

[73] Assignee: Buehler Ltd., Lake Bluff, Ill.

[21] Appl. No.: 439,997

[22] Filed: Nov. 8, 1982

[51] Int. Cl.³ .............................................. B25B 5/00
[52] U.S. Cl. ................................. 51/237 R; 51/131.1;
51/131.3; 403/348
[58] Field of Search ..... 51/237 R, 131.1, 131.3-131.4,
51/216 R, 216 T, 236, 375-379; 403/348, 349;
279/1 A, 1 B, 97, 9 R, 77, 78, 81; 81/177 R, 177
G; 285/401, 376, 360

[56] References Cited

U.S. PATENT DOCUMENTS

| | | | |
|---|---|---|---|
| 1,429,861 | 9/1922 | Flodin | 279/9 R |
| 1,972,086 | 9/1934 | Buckley | 51/237 R |
| 3,663,028 | 5/1972 | King, Jr. et al. | 279/1 B |
| 3,880,546 | 4/1975 | Segal | 403/349 |
| 4,020,600 | 5/1977 | Day | 51/237 R |

Primary Examiner—Frederick R. Schmidt
Assistant Examiner—Matthew D. Daschel
Attorney, Agent, or Firm—Charles F. Pigott, Jr.

[57] ABSTRACT

A chuck for suspending a specimen holder from a vertical drive shaft to permit the specimen holder to be rotated about the axis of the drive shaft and also pressed downwardly against an abrasive platen or the like which may also be rotated in the same or opposite direction, the chuck being biased to its locking position by a spring and being releasable through manual rotation of a sleeve member to overcome the spring force.

7 Claims, 7 Drawing Figures

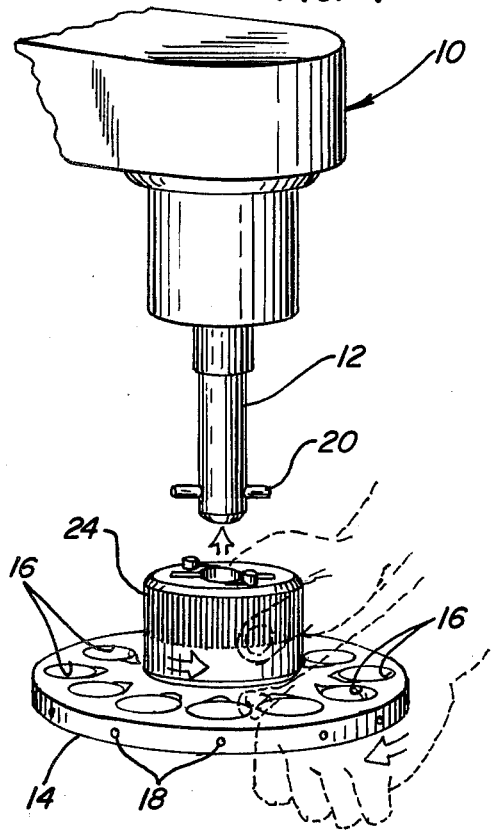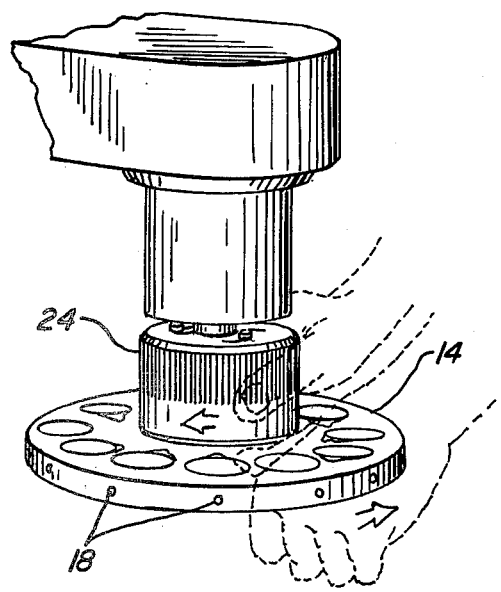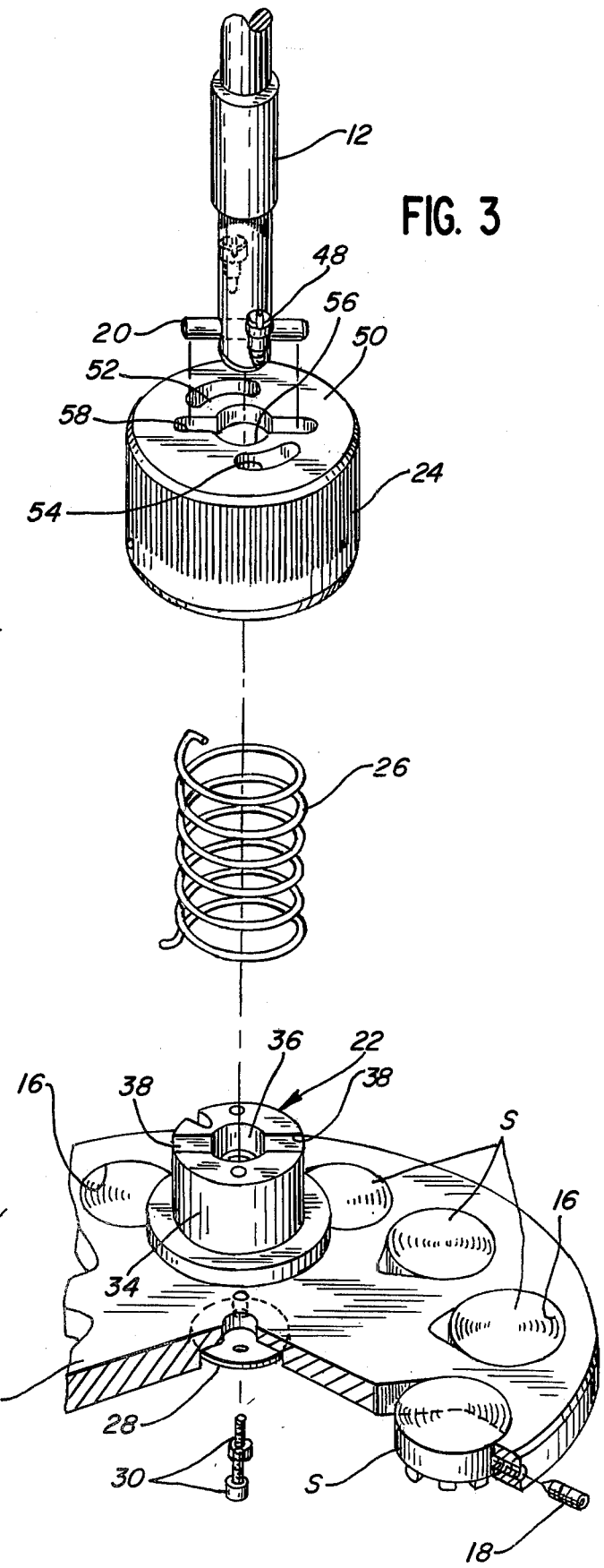

FIG. 4
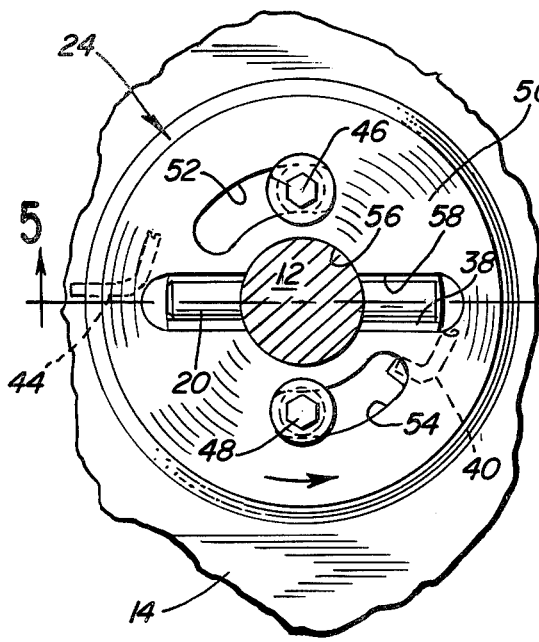
FIG. 5
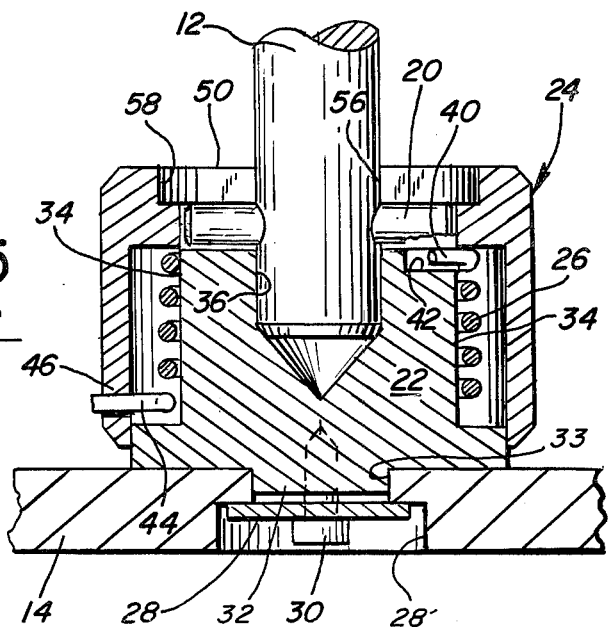
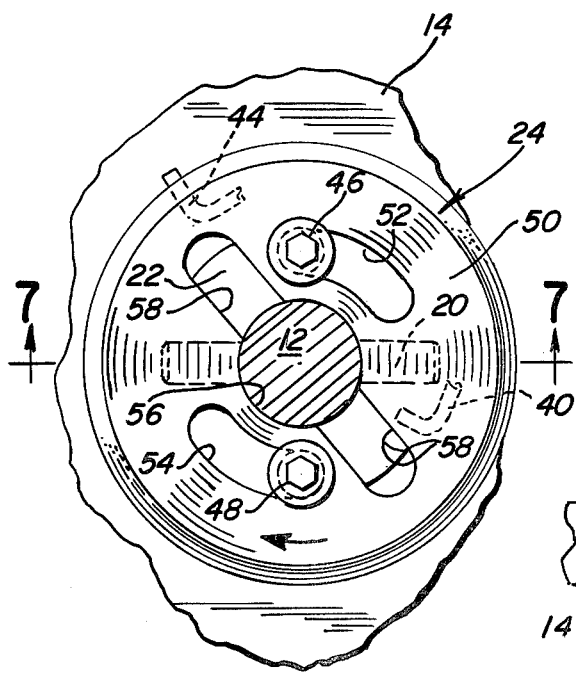
FIG. 6
FIG. 7

CHUCK FOR VERTICALLY HUNG SPECIMEN HOLDER

BRIEF SUMMARY OF THE INVENTION

The present invention relates to a chuck assembly for suspending a specimen holder from a vertical drive shaft to permit the specimen holder to be rotated and also pressed down against an abrasive platen or the like which may also be rotated. The purpose of such an operation is to grind or polish a plurality of metallurgical specimens or the like to prepare them for microscopic examination.

While various chuck assemblies are known in the art, such assemblies generally require that an operator perform a specific operation after locating a specimen holder in position for locking in order that positive locking of the specimen to a drive shaft is achieved. A safety hazard is thus presented if the operator fails to complete the final locking step to fully secure the chuck.

It is an object of the present invention to provide an improved chuck for securing a specimen holder in operative relation to a vertical drive shaft, including a spring-loaded rotatable sleeve which must be manually rotated to a release position to engage the chuck with a drive shaft, and thereafter is automatically locked upon release of the sleeve which is then rotated back to a locked position by spring means.

Another object of the invention is to provide improved means for connecting the chuck assembly to a specimen holder to permit slippage between them in the event of jamming of the specimen holder against an obstruction, the purpose being to avoid serious damage to the machine which drives the specimen holder.

The foregoing and other objects and advantages of the invention will be apparent from the following description of a preferred embodiment, taken in conjunction with the accompanying drawings.

DESCRIPTION OF THE DRAWINGS

FIG. 1 is a fragmentary perspective view showing the head of a polishing or grinding machine including a cross-pinned drive shaft, in combination with a chuck assembly which is attached to a specimen holder, the chuck being shown aligned beneath the drive shaft prior to being raised into engagement and locked thereto;

FIG. 2 is a perspective view similar to FIG. 1 showing the chuck assembly engaged and locked with the drive shaft;

FIG. 3 is an enlarged, exploded perspective view showing the cross-pinned drive shaft and specimen holder and the components of the chuck assembly for suspending the specimen holder from the drive shaft;

FIG. 4 is a fragmentary top plan view of the chuck assembly of the present invention showing the rotatable chuck sleeve rotated to its counter-clockwise open position against the bias of spring means which urges the sleeve to a clockwise locked position;

FIG. 5 is a vertical sectional view taken substantially along the line 5—5 of FIG. 4 and showing a fragmentary portion of a specimen holder which is frictionally secured to the underside of a base of the chuck assembly;

FIG. 6 is a top plan view similar to FIG. 4 showing the rotatable chuck sleeve in its clockwise locked position to which it is biased by spring means; and FIG. 7 is a vertical section view taken substantially along the line 7—7 of FIG. 6.

Now, in order to acquaint those skilled in the art with the manner of making and using my invention, I shall describe, in conjunction with the accompanying drawings, a preferred embodiment of the invention.

DETAILED DESCRIPTION OF THE INVENTION

Referring now to the drawings, FIG. 1 shows the head 10 of a polisher/grinder machine for preparing metallurgical specimens. The head 10 includes a drive shaft 12 which is rotatable for rotating a specimen holder 14. The polisher/grinder machine includes a rotatable horizontal platen (not shown) located beneath the drive shaft 12 and on which a grinding disc or the like may be mounted. The head 10 is movable vertically for the purpose of moving drive shaft 12 toward or away from the rotatable platen.

The polisher/grinder machine and the specimen holder 14 do not themselves comprise a part of the present invention. However, it is helpful in appreciating the utility of the chuck assembly of the present invention to understand the purpose and function of such a polisher/grinder and specimen holder. It will be noted the specimen holder 14 comprises a disc-shaped member having a plurality of round openings 16. Each such opening 16 is intended to receive a mounted specimen or sample S (see FIG. 3), namely, a metallurgical sample which has been mounted in a round block of plastic in known manner to facilitate the handling of the sample. Such a mounted sample S will have one face of the sample exposed so that it may be ground, polished or otherwise prepared for subsequent microscopic examination.

It will be understood with reference to FIGS. 1 and 3 that a mounted sample S may be placed in each of the openings 16 of the specimen holder and secured therein by a corresponding set screw 18 which communicates with the adjacent opening and serves to clamp a mounted sample. The mounted samples are placed in the openings 16 with the exposed surface of the sample facing downward so when the sample holder is mounted to the drive shaft as shown in FIG. 2, the exposed sample surfaces will face downwardly toward the rotatable abrasive platen (not shown).

After using the chuck of the present invention to suspend sample holder 14 from drive shaft 12 in a manner to be described hereinafter, the machine operator may initiate motor drive means to rotate the sample holder and the abrasive platen, in the same or opposite directions as desired, and to lower the head 10 to press the plurality of exposed sample surfaces down against the abrasive platen with a desired vertical pressure. In the foregoing manner, a plurality of mounted samples may be ground or polished in preparation for microscopic examination. There are known means not described herein for assuring that the plurality of samples are secured in sample holder 14 in coplanar fashion so that they are uniformly ground or polished during operation of the machine.

There will now be described the chuck assembly of the present invention for suspending sample holder 14 from drive shaft 12. I provide a cross pin 20 which extends transversely through drive shaft 12 adjacent the lower end thereof for cooperation with the chuck assembly. The chuck assembly includes a base 22 (see FIG. 3), a rotatable sleeve 24, a torsion spring 26 for biasing sleeve 24 in a clockwise direction as viewed in FIG. 3, and a washer 28 and screws 30 for frictionally securing the chuck assembly to the top of specimen holder 14.

The chuck base 22 (see FIG. 3) comprises a cylindrical body 34 having a bore 36 which extends down into the upper end of the body 34, and a slot 38 which extends diametrically across the body at the upper end thereto to a depth and length which at least slightly exceed the diameter and length of cross pin 20. As will be described more fully later herein slot 38 is intended to receive cross pin 20 when the chuck is engaged and locked to drive shaft 12.

The chuck base 22 has a centrally located round projection 32 formed on its bottom which is adapted to seat within a corresponding central recess 33 formed in the top of sample holder 14 (as best shown in FIGS. 5 and 7). In order to frictionally secure chuck base 22 to a sample holder such as the holder 14, there is provided washer 28 (see FIGS. 3 and 5) which sits in a circular recess 28' in the underside of the sample holder, and one or more screws 30 are passed through corresponding openings in washer 28 and in the base of the sample holder recess and are threaded into the underside of the chuck base 22, thereby frictionally securing chuck base 22 to the upper central portion of the sample holder 14.

As shown in FIGS. 5 and 6, torsion spring 26 is positioned over the outside of chuck body 34, and sleeve 24 is mounted over the chuck body outwardly of the torsion spring. The upper end 40 of the torsion spring extends inwardly into an opening 42 formed in the side of chuck body 34 near the upper end thereof, and a lower end 44 of the spring passes outwardly through an opening 46 in the wall of sleeve 24. In the foregoing manner, torsion spring 26 is connected between sleeve 24 and chuck body 34 to bias the sleeve in a clockwise direction as viewed in FIGS. 4 and 6.

A pair of shoulder screws 46 and 48 (best shown in FIGS. 4 and 6) are threaded into the upper end of chuck body 34 on a diameter thereof and project up through corresponding arcuate slots formed in the top wall 50 of sleeve 24. The arcuate slots 52 and 54 are formed on a common arc about the central axis of top wall 50, and engagement by the two screws 46 and 48 with the ends of the corresponding slots 52 and 54 defines the two limiting rotational positions of sleeve 24.

The top wall 50 of sleeve 24 is further provided with a central bore 56 which communicates with a slot 58 extending through wall 50 and across a diameter of the sleeve top wall. The slot 58 has a width approximately equal to the width of the diametral slot 38 formed in the top of chuck body 34, which width is greater than the diameter of cross pin 20. The slot 58 is also longer than the length of cross pin 20, so the latter can pass through slot 58 and be received in slot 38.

When sleeve 24 is manually rotated to its extreme counterclockwise position as shown in FIG. 4, with screws 46 and 48 engaged against the ends of their respective arcuate slots 52 and 54, slot 58 in top wall 50 of sleeve 24 is aligned with slot 38 in the top of chuck body 22. When the sleeve 24 is rotated to the foregoing release position, with the assembly of the chuck and sample holder 14 positioned beneath drive shaft 12 as shown in FIG. 1, the foregoing assembly may be raised as shown in FIG. 2 to a position where cross pin 20 has passed through slot 58 in the top wall 50 of sleeve 24 and is seated in slot 38 in the top of chuck body 22 (see FIGS. 2, 5 and 7). In the foregoing position, the lower end of the drive shaft 12 has passed through the central aperture 56 in the top of sleeve 24 and seats in central bore 36 in the top of chuck body 22.

When the assembly of the chuck and sample holder 14 has been raised as described above to the position shown in FIG. 2, an operator need only release sleeve 24 in order to effect locking of the chuck to the lower end of drive shaft 12. Upon release of sleeve 24, torsion spring 26 rotates the sleeve to its extreme clockwise position shown in FIG. 6 where screws 46 and 48 are engaged against the opposite ends of the corresponding arcuate slots 52 and 54. In the latter position of sleeve 24, the top wall 50 of sleeve 24 overlies cross pin 20 and traps the cross pin in the slot 38 in chuck body 22. Accordingly, the chuck is locked to lower end of drive shaft 12 through cross pin 20 both vertically and rotationally. The shaft may therefore rotate sample holder 14 as well as apply downward pressure thereto.

It is an important advantage of the present invention that the chuck locks automatically once the chuck sleeve 24 is manually rotated to its release position as shown in FIG. 4, the assembly is raised to seat the cross pin 20 in slot 38 of chuck base 22, and the operator releases the sleeve so it rotates to the clockwise or locked position of FIG. 6. The foregoing provides an important safety feature, because it is impossible for an operator to forget to carry out a final locking operation.

A further advantage of the invention is the connection between the sample holder 14 and the chuck assembly. As shown in FIGS. 3, 5 and 7, the washer 28 and two screws 30 serve to frictionally clamp the sample holder 14 to the underside of the chuck base 22 in a manner so that, if during a polishing or grinding operation the sample holder encounters an obstruction which interferes with its rotation, it is possible for the sample holder 14 to slip relative to chuck base 22 for the purpose of preventing damage to the head 10 and associated grinder/polisher machine.

In the preferred embodiment described herein, the angle of rotation of chuck sleeve 24 is approximately 55 degrees, and the sleeve is biased to closed position by spring 26 which is torqued to 14 inch-pounds and is opened at a force of 20 inch-pounds.

During operation of the chuck described herein, as during polishing or grinding of a plurality of specimens mounted in plastic mounts, such as the mounted specimens S shown in FIG. 3, drive shaft 12 will normally be rotating and simultaneously pressing down on a sample holder 14. It is therefore important that the cross pin 20 fit snugly in the slot 38 formed in the top of the chuck base 22. It is not necessary that the top wall 50 of sleeve 24 fit tightly over the cross pin 20, although a relatively close fit as shown in FIG. 7 is desirable.

What is claimed is:

1. A chuck assembly for suspending a work holder from a vertical drive shaft having a horizontal cross pin adjacent its lower end, said chuck assembly comprising, in combination, a generally cylindrical chuck body having a recess in its upper end including a transverse recess portion for receiving the lower end of said drive shaft with said cross pin seated in said transverse recess portion, a rotatable sleeve mounted over said body including a sleeve top wall which overlies the top of said body, a central opening including a transverse slot in said sleeve top wall which is dimensioned to permit passage therethrough of said drive shaft and cross pin, said sleeve being rotatable relative to said body between an open position where said transverse slot is aligned with said transverse recess portion to permit said cross pin to pass through said slot and be seated in said recess, and a locked position where said transverse slot is out of alignment with said transverse recess portion so said sleeve top wall overlies and traps a cross pin seated in said transverse recess, stop means for defining the open and locked positions of said rotatable sleeve, and spring means for biasing said rotatable sleeve to said locked position.

2. A chuck assembly as defined in claim 1 where said spring means comprises a torsion spring having one end connected to said sleeve and its other end connected to said chuck body.

3. A chuck assembly as defined in claim 1 where said stop means comprise an arcuate slot formed in said sleeve top wall, and fixed stop means secured to the top of said body and projecting up through said arcuate slot whereby said open and locked positions are defined through engagement of said fixed stop means with an end of said arcuate slot.

4. A chuck assembly as defined in claim 1 including attachment for connecting a work holder to the underside of said chuck body by frictionally clamping the same, whereby during rotation of said chuck assembly and work holder by said drive shaft there is permitted slippage between said work holder and chick body if said work holder encounters an obstruction.

5. A chuck assembly as defined in claim 4 where said attachment means comprises washer means frictionally pressed against the underside of a work holder and positively connected to the underside of said chuck body to frictionally clamp said work holder between said washer means and said chuck body.

6. A chuck assembly for suspending a work holder from a vertical drive shaft having a horizontal cross pin adjacent its lower end, said chuck assembly comprising, in combination, a generally cylindrical chuck body having a recess in its upper end including a transverse recess portion for receiving the lower end of said drive shaft with said cross pin seated in said transverse recess portion, a rotatable sleeve mounted over said body including a sleeve top wall which overlies the top of said body, a central opening including a transverse slot in said sleeve top wall which is dimensioned to permit passage therethrough of said drive shaft and cross pin, said sleeve being rotatable relative to said body between an open position where said transverse slot is aligned with said transverse recess portion to permit said cross pin to pass through said slot and be seated in said recess, and a locked position where said transverse slot is out of alignment with said transverse recess portion so said sleeve top wall overlies and traps a cross pin seated in said transverse recess, an arcuate slot formed in said sleeve top wall, fixed top means secured to the top of said body and projecting up through said arcuate slot whereby said open and locked positions are defined through engagement of said fixed stop means with an end of said arcuate slot, and a torsion spring having one end connected to said sleeve and its other end connected to said chuck body for biasing said rotatable sleeve to said locked position.

7. A chuck assembly as defined in claim 6 including frictional washer means frictionally pressed against the underside of a work holder and positively connected to the underside of said chuck body to frictionally clamp said work holder between said washer means and said chuck body, whereby during rotation of a work holder by said drive shaft slippage is permitted between said work holder and chuck body if said work holder encounters an obstruction.

* * * * *